United States Patent
Mirda (10) Patent No.: US 9,848,920 B2
(45) Date of Patent: Dec. 26, 2017

(54) SPINAL IMPLANT SYSTEM AND METHOD

(71) Applicant: Warsaw Orthopedic, Inc., Warsaw, IN (US)

(72) Inventor: James M. Mirda, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 302 days.

(21) Appl. No.: 14/248,079

(22) Filed: Apr. 8, 2014

(65) Prior Publication Data

US 2015/0282845 A1 Oct. 8, 2015

(51) Int. Cl.
*A61B 17/70* (2006.01)

(52) U.S. Cl.
CPC ...... *A61B 17/7055* (2013.01); *A61B 17/7032* (2013.01); *A61B 17/7007* (2013.01)

(58) Field of Classification Search
CPC ............ A61B 17/7055; A61B 17/7007; A61B 17/7032
See application file for complete search history.

(56) References Cited

U.S. PATENT DOCUMENTS

| | | | | |
|---|---|---|---|---|
| 5,498,262 A | * | 3/1996 | Bryan | A61B 17/1757 606/250 |
| 5,531,747 A | * | 7/1996 | Ray | A61B 17/7055 606/278 |
| 5,645,544 A | * | 7/1997 | Tai | A61B 17/7037 606/259 |
| 5,947,965 A | * | 9/1999 | Bryan | A61B 17/1757 606/250 |
| 6,001,098 A | * | 12/1999 | Metz-Stavenhagen | A61B 17/7035 606/264 |
| 2002/0042614 A1 | * | 4/2002 | Ueyama | A61B 17/7002 606/261 |
| 2011/0034957 A1 | * | 2/2011 | Biedermann | A61B 17/7035 606/305 |
| 2012/0150232 A1 | * | 6/2012 | Van Nortwick | A61B 17/7001 606/264 |
| 2012/0179205 A1 | * | 7/2012 | Miller | A61B 17/7055 606/264 |
| 2013/0184760 A1 | * | 7/2013 | Ballard | A61B 17/7041 606/278 |
| 2013/0211457 A1 | * | 8/2013 | Dickinson | A61B 17/7055 606/264 |
| 2013/0245690 A1 | * | 9/2013 | Bridwell | A61B 17/7038 606/278 |
| 2014/0257399 A1 | * | 9/2014 | Rezach | A61B 17/7037 606/272 |
| 2014/0277146 A1 | * | 9/2014 | Li | A61B 17/7052 606/252 |

FOREIGN PATENT DOCUMENTS

FR  EP 0553042 A1 * 7/1993  ......... A61B 17/7002

\* cited by examiner

*Primary Examiner* — Ellen C Hammond (57) ABSTRACT

A spinal construct comprises a fastener attached with sacral and/or pelvic tissue of a body. A connector is selectively movable in a coronal plane relative to the body. The connector has a first end connected with the fastener and a second end having a locking surface engageable with an implant. A lock element is engageable with the connector and defines an implant cavity. Systems and methods are disclosed.

20 Claims, 8 Drawing Sheets

SPINAL IMPLANT SYSTEM AND METHOD

TECHNICAL FIELD

The present disclosure generally relates to surgical implants for the treatment of spinal disorders, and more particularly to a surgical system and method for treatment of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods, connectors and plates can be used to provide stability to a treated region. During surgical treatment, one or more rods may be attached via fasteners and connectors to the exterior of two or more vertebral members to provide stability to a treated region. Fasteners may also be attached to iliac bone. This disclosure describes an improvement over these prior art technologies.

SUMMARY

In one embodiment, a spinal construct is provided. The spinal construct comprises a fastener attached with sacral and/or pelvic tissue of a body. A connector is selectively movable in a coronal plane relative to the body. The connector has a first end connected with the fastener and a second end having a locking surface engageable with an implant. A lock element is engageable with the connector and defines an implant cavity. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system and method for treatment of a spine disorder. In one embodiment, the systems and methods of the present disclosure are employed with a spinal joint fusion, for example, with a cervical, thoracic, lumbar and/or sacral region of a spine.

In one embodiment, the present disclosure provides a surgical system including a spinal construct configured to allow for coronal adjustability, such as, for example, in a sacro-pelvic region. In one embodiment, the spinal construct includes a connector that allows for coronal adjustability. In one embodiment, a spinal construct is configured to allow for coronal adjustability to facilitate assembly of the construct including a rod extending from a lumbar spine to an iliac and/or sacro-iliac screw.

In one embodiment, the surgical system includes a spinal construct having intra-operative flexibility in assembly by being configured to mix and match different receivers for engaging the rod with different post diameters of the connector. In some embodiments, the surgical system includes a spinal construct having an intraoperative flexibility configuration that reduces inventory requirements. In one embodiment, the surgical system includes a spinal construct including a connector having circumferential splines that engage the rod in a locking orientation. In one embodiment, the surgical system includes a spinal construct having a low profile configuration with vertebrae including sacral tissue and/or pelvic tissue. In one embodiment, the surgical system includes a spinal construct having an offset connector with coronal adjustability.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.) thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Figure 13:
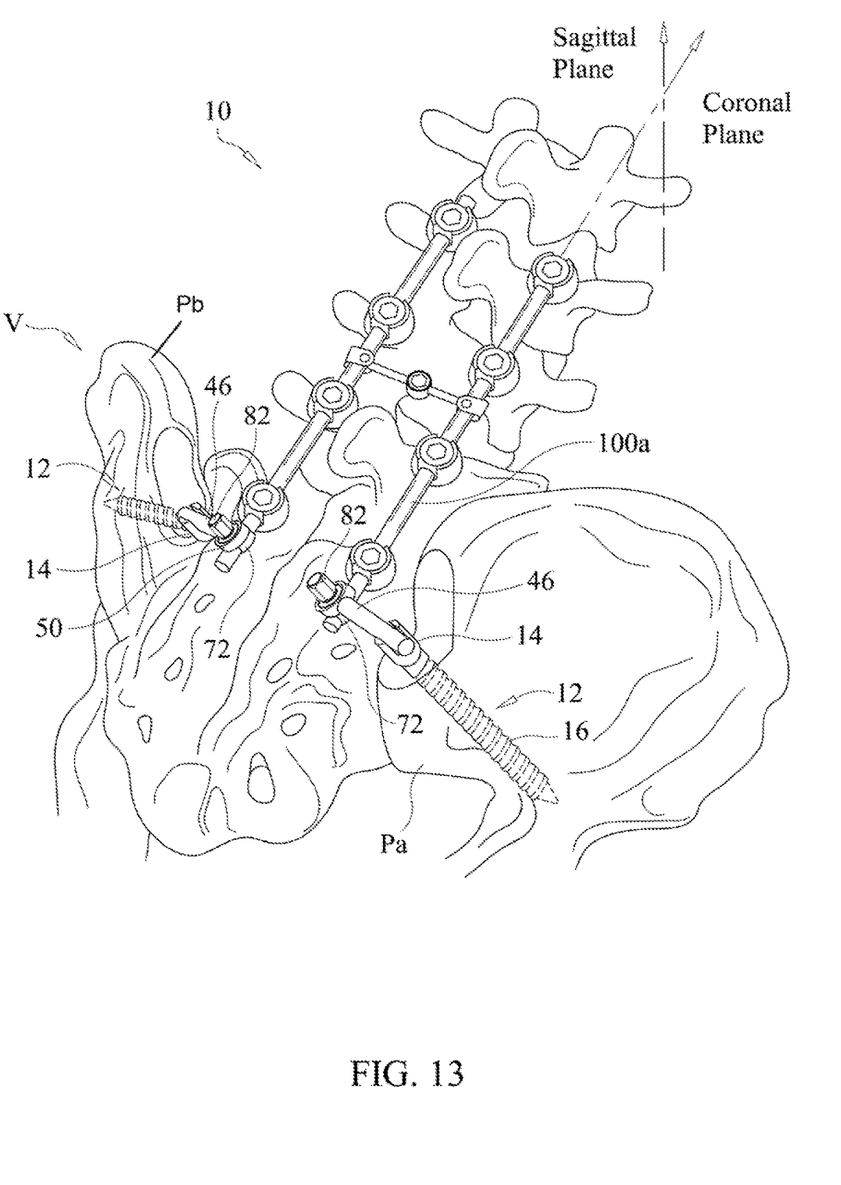
FIG. 13 is a perspective view of components of one embodiment of a system in accordance with the principles of the present disclosure disposed with a body.

Spinal implant system 10 may be employed, for example, with minimally invasive procedures, including percutaneous techniques, mini-open surgical techniques and/or open surgical techniques to deliver and introduce instrumentation and/or implants, such as, for example, a spinal construct, at a surgical site within a subject body of a patient, which includes, for example, a spine having vertebrae V, as shown, for example, in FIG. 13. In some embodiments, the spinal constructs can include one or more bone fasteners, spinal rods, connectors and/or plates.

Figure 1:
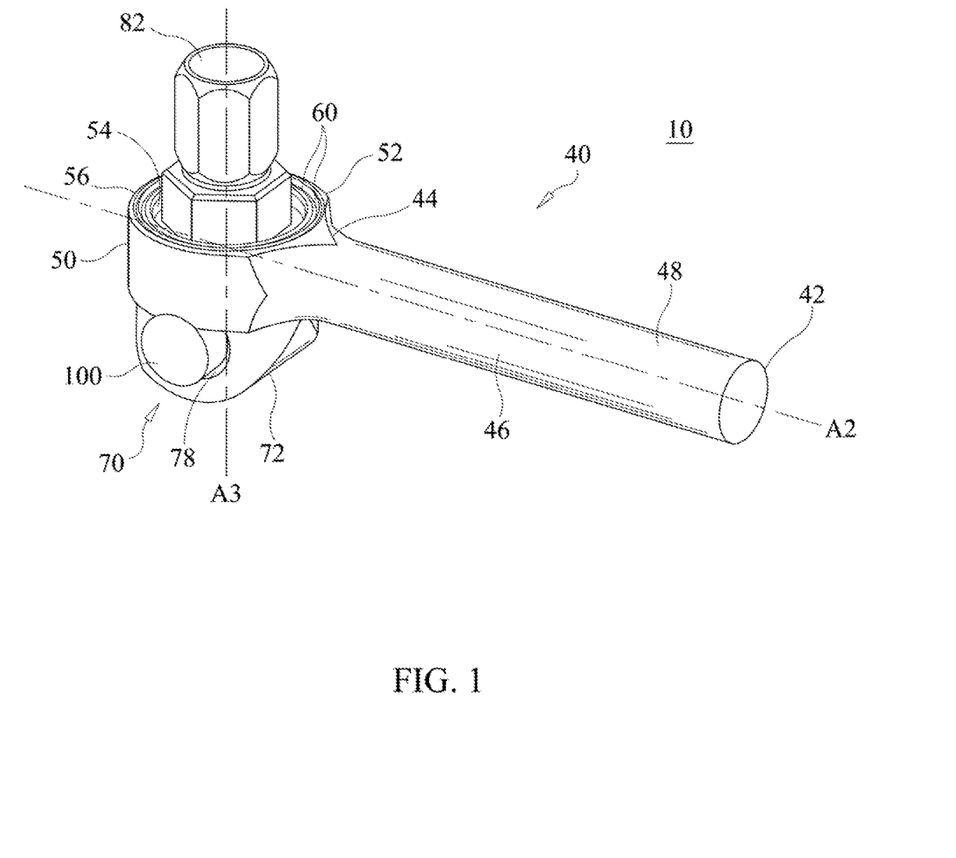
FIG. 1 is a perspective view of components of one embodiment of a system in accordance with the principles of the present disclosure.
Figure 2:
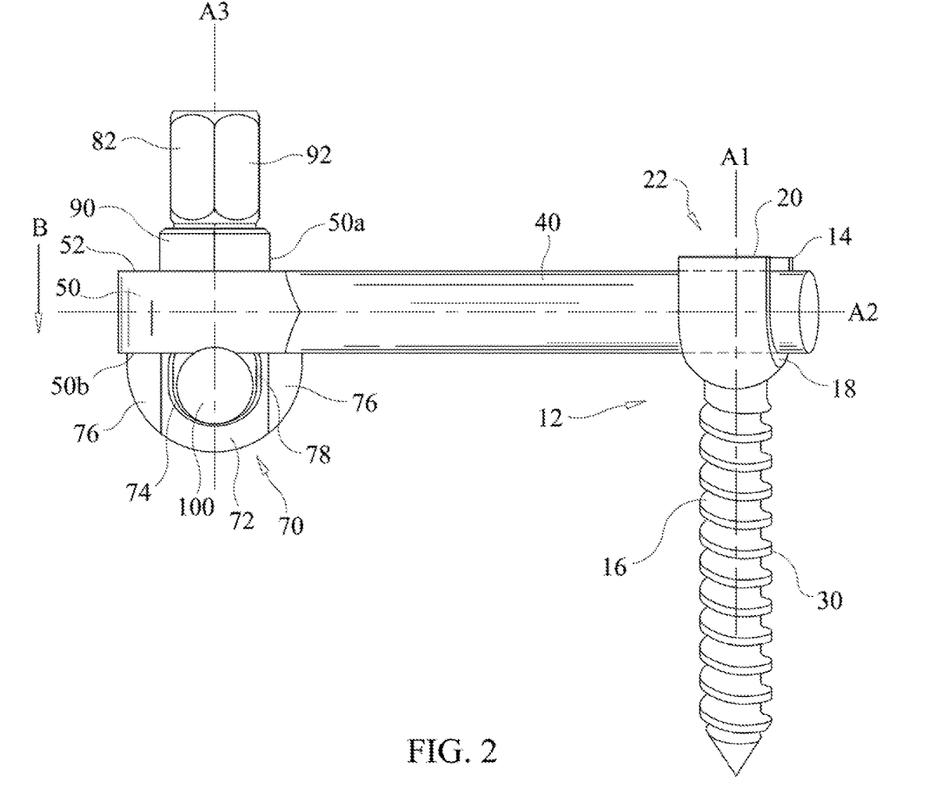
FIG. 2 is a side view of components of the system shown in FIG. 1.
Figure 3:
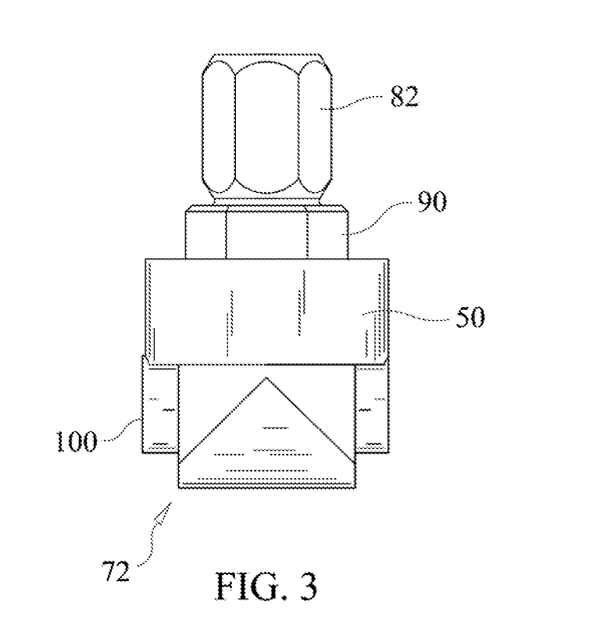
FIG. 3 is a side view of the components shown in FIG. 1.
Figure 4:
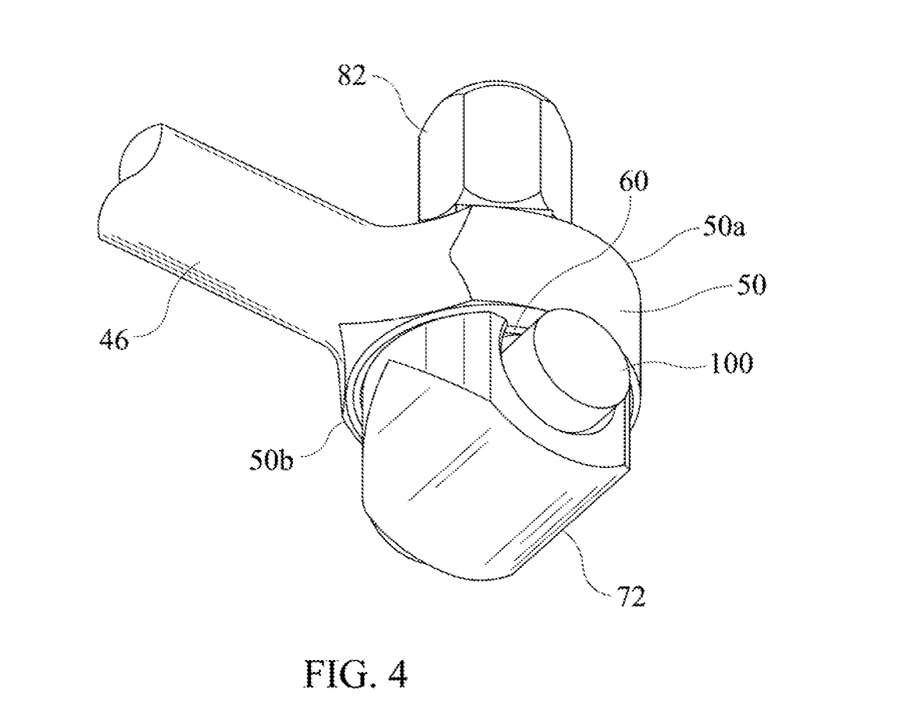
FIG. 4 is a break away view of the components shown in FIG. 1.

Spinal implant system 10 includes a spinal construct comprising a fastener 12 including a first portion, such as, for example, a receiver 14 and a second portion configured to penetrate tissue, such as, for example, a shaft 16, as shown in FIG. 2. Receiver 14 defines a longitudinal axis A1 and includes a pair of spaced apart arms 18, 20 that each extends parallel to axis A1. Arms 18, 20 define a U-shaped implant cavity 22 therebetween configured for disposal of a spinal implant, such as, for example, a connector, as described herein. Cavity 22 extends perpendicular to axis A1. In some embodiments, cavity 22 may have various cross section configurations, such as, for example, oval, oblong, triangular, rectangular, square, polygonal, irregular, uniform, non-uniform, variable, tubular and/or tapered. In some embodiments, arm 18, arm 20 and/or cavity 22 may be disposed at alternate orientations, relative to axis A1, such as, for example, transverse, perpendicular and/or other angular orientations such as acute or obtuse, co-axial and/or may be offset or staggered. In some embodiments, receiver 14 may be dosed to define a closed cavity 22. In some embodiments, a coupling member, such as, for example, a set screw may engage receiver 14 to fix and/or lock the spinal implant with receiver 14.

Shaft 16 is configured with a cylindrical cross section and includes an outer surface 30 having an external thread form. In some embodiments, the thread form on surface 30 may include a single thread turn or a plurality of discrete threads. In some embodiments, the thread form on surface 30 may be self-tapping or intermittent, or may have more than one crest winding about shaft 16. In some embodiments, other engaging structures may be disposed on shaft 16, such as, for example, a nail configuration, barbs, expanding elements, raised elements and/or spikes to facilitate engagement of the shaft with tissue, such as, for example, vertebrae. In some embodiments, all or only a portion of shaft 16 may have alternate cross section configurations, such as, for example, oval, oblong, triangular, square, polygonal, irregular, uniform, non-uniform, offset, staggered, undulating, arcuate, variable and/or tapered. In some embodiments, all or only a portion of surface 30 may have alternate surface configurations to enhance fixation with tissue such as, for example, rough, arcuate, undulating, mesh, porous, semi-porous, dimpled and/or textured. In some embodiments, all or only a portion of shaft 16 may be cannulated.

A connector 40 extends between an end 42 and an end 44. Connector 40 is configured for selective rotation relative to an implant in a coronal plane of a body and/or vertebrae, such as, for example, that shown in FIG. 13, such that connector 40 is in alignment with receiver 14 of fastener 12, as discussed herein. End 42 includes an extension 46 that defines an axis A2. Extension 46 is configured for disposal with receiver 14. In some embodiments, all or only a portion of extension 46 may have alternate cross section configurations, such as, for example, oval, oblong, triangular, square, polygonal, irregular, uniform, non-uniform, offset, staggered, undulating, arcuate, variable and/or tapered. Extension 46 includes an outer surface 48. Surface 48 may have alternate surface configurations to enhance fixation with receiver 14 such as, for example, rough, arcuate, undulating, mesh, porous, semi-porous, dimpled and/or textured.

End 44 includes a surface, such as, for example, a disc 50. In some embodiments, all or only a portion of disc 50 may have alternate cross section configurations, such as, for example, oval, oblong, triangular, square, polygonal, irregular, uniform, non-uniform, offset, staggered, undulating, arcuate, variable and/or tapered. Disc 50 has a side 50a and a side 50b. Disc 50 is configured for disposal in a coronal plane, as described herein. Disc 50 includes an inner surface 54 that defines a cavity, such as, for example, a passageway 55 extending between side 50a and side 50b. Passageway 55 defines an axis A3 disposed transverse to axis A2.

Figure 5:
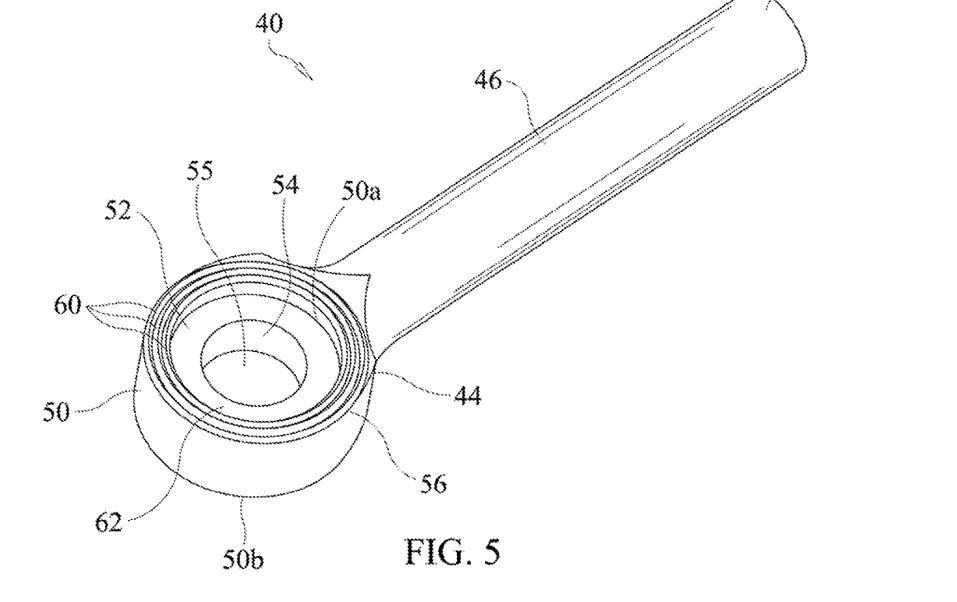
FIG. 5 is a perspective view of components of one embodiment of a system in accordance with the principles of the present disclosure.
Figure 6:
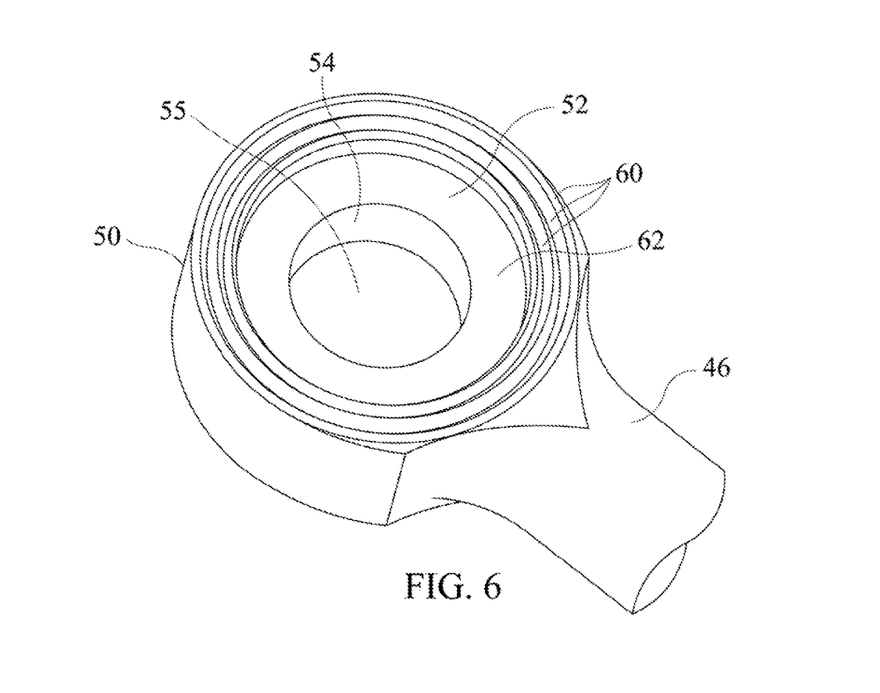
FIG. 6 is a break away view of the components shown in FIG. 5.
Figure 7:
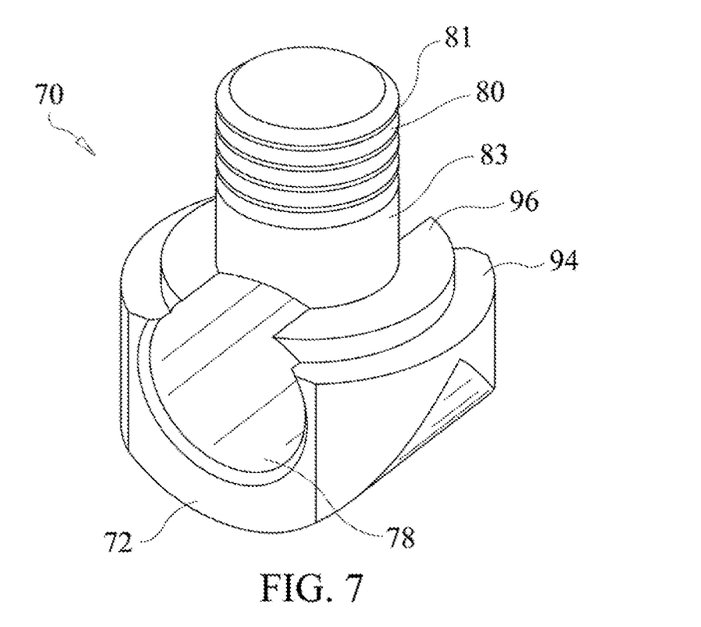
FIG. 7 is a perspective view of components of one embodiment of a system in accordance with the principles of the present disclosure.
Figure 8:
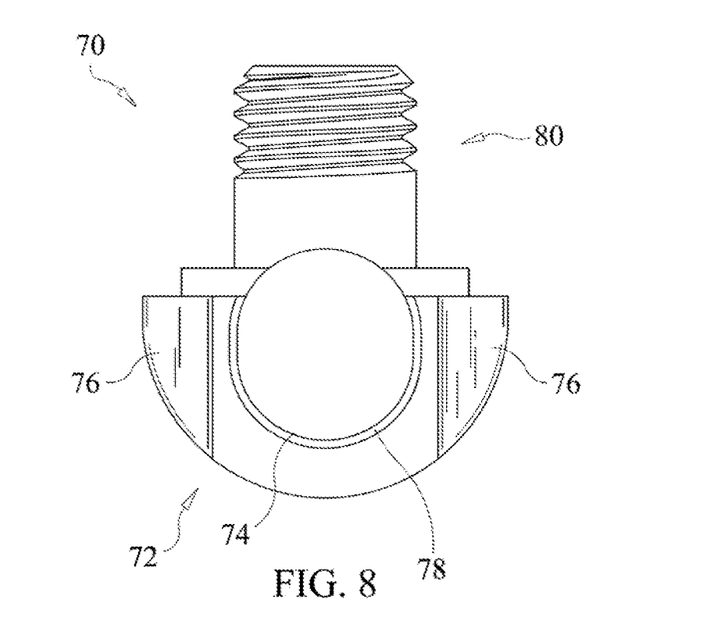
FIG. 8 is a side view of the components shown in FIG. 7.
Figure 9:
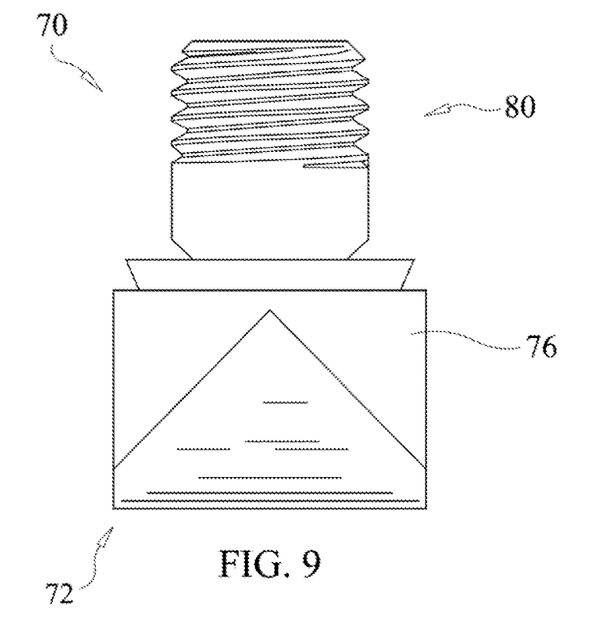
FIG. 9 is a side view of the components shown in FIG. 7.
Figure 10:
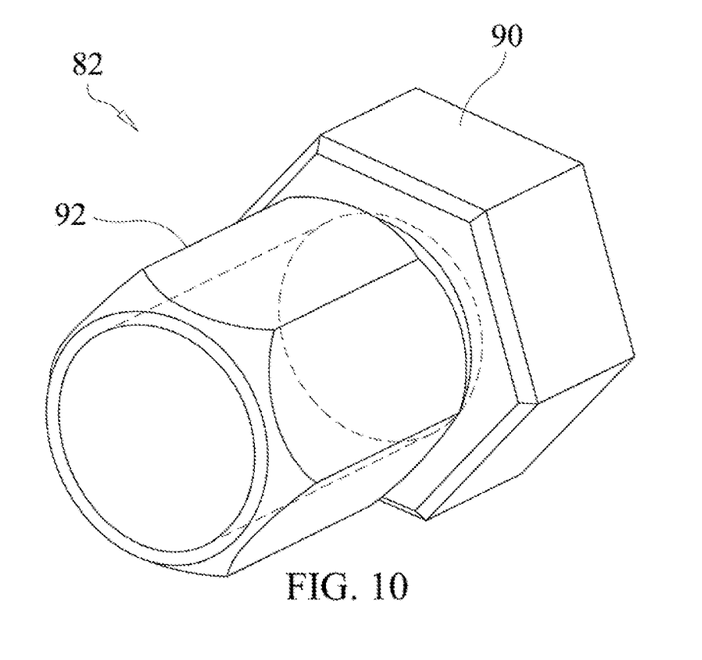
FIG. 10 is a perspective view of components of one embodiment of a system in accordance with the principles of the present disclosure.
Figure 11:
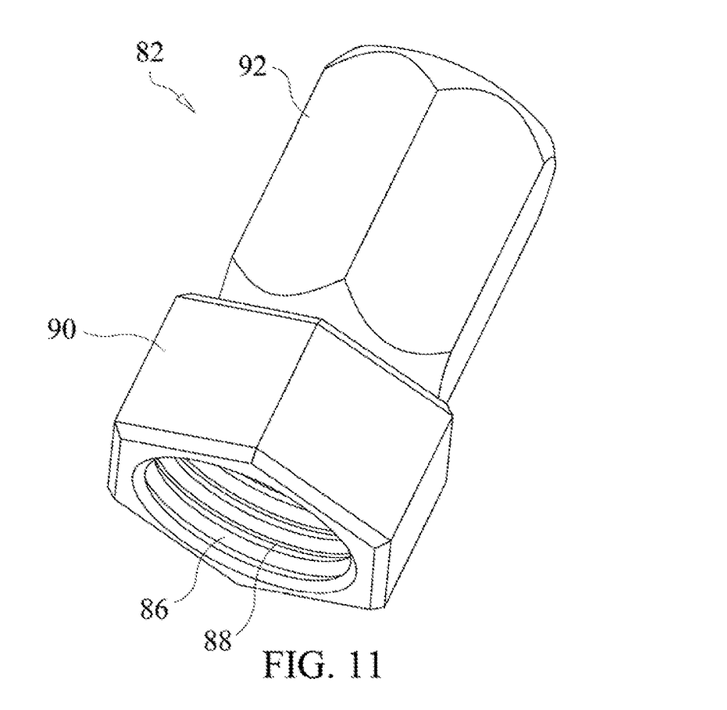
FIG. 11 is a perspective view of the components shown in FIG. 10.
Figure 12:
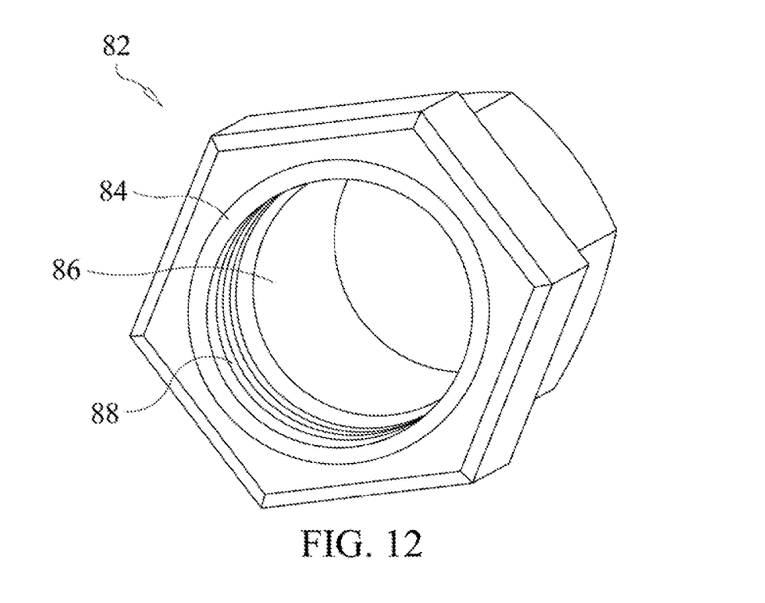
FIG. 12 is a perspective view of the components shown in FIG. 10.

Side 50a and side 50b each include a planar surface 52. Surface 52 defines a locking surface 56. In one embodiment, as shown in FIG. 5, locking surface 56 includes a plurality of circumferential ridges, such as, for example, splines 60. Splines 60 are disposed in an increasing radial orientation about surface 52. Surface 52 may have alternate surface configurations to enhance fixation, such as, for example, rough, arcuate, undulating, mesh, porous, semi-porous, dimpled and/or textured. In some embodiments, surface 52 can include various locking elements, such as, for example, frictional engagement, mutual grooves, screws, adhesive, nails, barbs and/or raised elements. Surface 52 and splines 60 define a cavity 62 that extends around passageway 55. Cavity 62 is configured for disposal of a portion of a lock element, as described herein.

A lock element 70 is engageable with connector 40. Lock element 70 includes a receiver 72. Receiver 72 includes a surface 74 that defines spaced arms 76. Arms 76 define a U-shaped implant cavity 78. Cavity 78 is configured for disposal of an implant, such as, for example, a spinal rod, as described herein. In some embodiments, connector 40 can be employed with one or a plurality of alternately configured receivers to accommodate, for example, differently configured and/or diameter spinal rods. In some embodiments, all or only a portion of receiver 72 may have alternate cross section configurations, such as, for example, oval, oblong, triangular, square, polygonal, irregular, uniform, non-uniform, offset, staggered, undulating, arcuate, variable and/or tapered.

Receiver 72 includes a mating part, such as, for example, a shaft 80. Shaft 80 includes a threaded portion 81 configured for engagement with a mating part, such as, for example, a nut, as described herein. Shaft 80 includes a non-threaded portion 83 configured for engagement with surface 54. In some embodiments, a thread form of portion 81 may include a single thread turn or a plurality of discrete threads. In some embodiments, all or only a portion of shaft 80 may have alternate cross section configurations, such as, for example, oval, oblong, triangular, square, polygonal, irregular, uniform, non-uniform, offset, staggered, undulating, arcuate, variable and/or tapered.

Receiver 72 includes a mating part, such as, for example, a nut 82. Nut 82 includes an inner surface 84 that defines a cavity 86. Surface 84 includes a threaded surface 88 configured for engagement with shaft 80. Nut 82 includes an outer surface 90 configured for engagement with a tool, such as, for example, a driver. In some embodiments, surface 90 may have various cross section configurations, such as, for example, cylindrical, oval, oblong, triangular, rectangular, square, hexagonal, polygonal, irregular, uniform, non-uniform, variable and/or tapered. Nut 82 includes a flange 92 configured for break off after assembly such that a profile of the construct is reduced. Nut 82 is configured to lock a spinal rod with receiver 72, as described herein.

Receiver 72 includes a surface 94 configured for engagement with disc 50. Surface 94 includes a raised surface portion 96 configured for nested engagement with surface 52 and disposal in cavity 62. In some embodiments, this configuration allows disc 50 to provisionally resist and/or prevent translation of a spinal rod relative to disc 50.

The spinal construct includes a spinal rod 100 configured for disposal with receiver 72. In some embodiments, spinal rod 100 may have a semi-rigid, rigid or elastic configuration, and/or have elastic properties, such as the elastic properties corresponding to the material examples described above. In some embodiments, spinal rod 100 can include a plurality of separately attachable or connectable portions or sections, or may be monolithically formed as a single continuous element. The spinal construct can include one or a plurality of spinal rods. In some embodiments, spinal rod 100 is configured to extend over one or a plurality of vertebral levels.

Spinal rod 100 can have a uniform thickness/diameter. In some embodiments, spinal rod 100 may have various surface configurations, such as, for example, rough, threaded for connection with surgical instruments, arcuate, undulating, porous, semi-porous, dimpled, polished and/or textured. In some embodiments, the thickness defined by spinal rod 100 may be uniformly increasing or decreasing, or have alternate diameter dimensions along its length. In some embodiments, spinal rod 100 may have various cross section configurations, such as, for example, oval, oblong, triangular, rectangular, square, polygonal, irregular, uniform, non-uniform, variable and/or tapered.

In assembly, operation and use, spinal implant system 10, similar to the systems and methods described herein, is employed with a surgical procedure, as described herein, for treatment of a condition or injury of an affected section of the spine including vertebrae V, as shown in FIG. 13.

In use, to treat the affected section of the spine, a medical practitioner obtains access to a surgical site including vertebrae V and/or a sacro-pelvic region of a body in any appropriate manner, such as through incision and retraction of tissues. System 10 may be used in any existing surgical method or technique including open surgery, mini-open surgery, minimally invasive surgery and percutaneous surgical implantation, whereby portions of vertebrae V and/or a sacro-pelvic region of a body are accessed through one or more micro-incisions, or sleeves that provide a protected passageway to the area. Once access to the surgical site is obtained, the particular surgical procedure is performed for treating the spinal disorder. System 10 is employed to augment the surgical treatment. One or more of the components of system 10 can be delivered or implanted as a pre-assembled device or can be assembled in situ.

Components of system 10, including rods 100a and 100b, similar to rod 100 described above, are connected with vertebrae V including lumbar vertebrae and the sacrum via bone fasteners. Rods 100a, 100b are coupled to the bone fasteners via set screws. Pilot holes are made in a sacro-pelvic region, such as, for example, ilium Pa and ilium Pb adjacent rods 100a, 100b. Fasteners 12, as described herein, are aligned with the plot holes and fastened with the tissue of ilium Pa and ilium Pb adjacent rods 100a, 100b.

Rods 100a, 100b are manipulated for disposal in cavity 78 of receiver 72 such that rods 100a, 100b are each disposed between arms 76 of disc 50, as described herein. Each connector 40 is positioned, laterally and contra-laterally for bi-lateral placement, with side 50b facing lock element 70, as shown in FIG. 2. Connector 40 is translated over shaft 80, as shown by arrow B, into a position such that extension 46 extends towards fastener 12. Shaft 80 is positioned in passageway 55 such that surface 83 is disposed in passageway 55 and surface 81 extends through passageway 55 beyond side 50a.

Each surface 96 is disposed in cavity 62 such that side 50b is in contact with each of spinal rods 100a, 100b, respectively. End 42 is disposed in cavity 22 and nut 82 is provisionally engaged with portion 81 of shaft 80. Splines 60 engage the surface of each of rods 100a, 100b. Each connector 40 is selectively manipulated for adjustment of extension 46 within the coronal plane such that axis A2 is rotated relative to and about axis A3. Connector 40 is positioned such that end 42 is selectively aligned for disposal within cavity 22 of receiver 14. Rotation of each connector 40 relative to respective rods 100a, 100b provides for selective positioning of extension 46 such that extension 46 is selectively aligned with and disposed in receiver 14.

End 42 is disposed in cavity 22 in the selected alignment of extension 46 with fastener 12 in the coronal plane and nut 82 is engaged with portion 81 of shaft 80 to lock the components of system 10 in the selected alignment. An instrument (not shown) engages each surface 90 to rotate nut 82 and lock each connector 40 with lock element 70 to fixedly secure rods 100a, 100b with discs 50, respectively. Each flange 90 is engaged with an instrument (not shown) to reach a torque limit break off, as described herein, to fix the spinal rods 100a, 100b with connectors 40 and fasteners 12 in the selected alignment and reduce the profile with vertebrae V and/or the sacro-pelvic region of the body.

Upon completion of the procedure, the surgical instruments, assemblies and non-implanted components of spinal implant system 10 are removed and the incision is dosed. Spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, spinal implant system 10 includes one or more fasteners, not shown, for attaching a spinal construct with tissue, as described herein. In some embodiments, the fasteners may be engaged with tissue in various orientations, such as, for example, series, parallel, offset, staggered and/or alternate vertebral levels. In some embodiments, one or more of the fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
  a fastener configured to be attached with sacral and/or pelvic tissue of a body, the fastener comprising an inner surface defining a connector cavity;
  a connector configured to be selectively movable in a coronal plane relative to the body, the connector having a first end with an even outer surface that engages the inner surface and a second end having a locking surface engageable with an implant, the second end comprising a passageway that extends through the locking surface and an opposite bottom surface of the second end; and
  a lock element including a receiver having spaced apart arms that define a portion of an implant cavity, the receiver comprising a raised portion between the arms and a cylindrical shaft that extends from the raised portion, end surfaces of the arms engaging the bottom surface such that the raised portion is nested within the passageway, the shaft comprising a threaded portion and a non-threaded portion that is positioned within the passageway, an inner surface of the non-threaded portion defining a portion of the implant cavity.

2. A spinal construct as recited in claim 1, wherein the lock element includes a nut engageable with the threaded portion.

3. A spinal construct as recited in claim 1, wherein the receiver includes one of a plurality of alternately configured receivers.

4. A spinal construct as recited in claim 1, wherein the first end includes an extension defining a first axis and the locking surface includes a planar surface disposed in the coronal plane.

5. A spinal construct as recited in claim 4, wherein the planar surface includes an inner surface that defines the passageway, the passageway defining a second axis disposed transverse relative to the first axis.

6. A spinal construct as recited in claim 1, wherein the locking surface includes at least one ridge.

7. A spinal construct as recited in claim 1, wherein the locking surface includes a plurality of ridges that each extend circumferentially about the passageway.

8. A spinal construct as recited in claim 1, wherein the locking surface includes a plurality of circumferential ridges disposed radially about the passageway in an increasing radial orientation.

9. A spinal construct as recited in claim 1, wherein the locking surface includes splines disposed in an increasing radial orientation about the locking surface.

10. A spinal construct as recited in claim 1, wherein the connector is selectively rotatable.

11. A spinal construct as recited in claim 1, wherein the connector is selectively rotatable relative to the implant in the coronal plane for alignment with a receiver of the fastener.

12. A spinal construct as recited in claim 1, wherein the connector includes a wall having a thickness from the locking surface to the bottom surface.

13. A spinal construct as recited in claim 1, wherein the implant cavity includes first and second sections that each have a U-shaped cross section and a third section between the first and second sections that has a circular cross section.

14. A spinal construct as recited in claim 1, wherein the non-threaded portion engages an inner surface of the second end that defines the passageway.

15. A spinal construct comprising:
a fastener configured to be attached with sacral and/or pelvic tissue of a body, the fastener comprising an inner surface defining a connector cavity;
a connector having an extension with an even outer surface that engages the inner surface and a disc having a locking surface engageable with an implant that is configured to be attached with vertebrae, the disc comprising a passageway that extends through the locking surface and an opposite bottom surface of the disc; and
a lock element engageable with the connector and including a receiver having spaced arms that define a portion of an implant cavity, the receiver comprising a raised portion between the arms and a cylindrical shaft that extends from the raised portion, end surfaces of the arms engaging the bottom surface such that the raised portion is nested within the passageway, the shaft comprising a threaded portion and a non-threaded portion that is positioned within the passageway, an inner surface of the non-threaded portion defining a portion of the implant cavity,
wherein the connector is selectively rotatable relative to the implant in a coronal plane for alignment with the fastener.

16. A spinal construct as recited in claim 15, wherein the lock element comprises a nut engageable with the non-threaded portion.

17. A spinal construct as recited in claim 15, wherein the receiver includes one of a plurality of alternately configured receivers.

18. A spinal construct as recited in claim 15, wherein the locking surface includes a plurality of ridges that each extend circumferentially about the passageway.

19. A spinal construct as recited in claim 15, wherein the locking surface includes splines disposed in an increasing radial orientation about the locking surface.

20. A spinal construct comprising:
a fastener comprising a threaded shank and a head having an inner surface defining a connector cavity;
a connector having an extension with an even outer surface that engages the inner surface and a disc having opposite top and bottom surfaces and a passageway that extends through the top and bottom surfaces, the top and bottom surfaces each comprising a planar portion and a locking portion, the locking portions each comprising splines disposed in an increasing radial orientation about the passageway, the planar portion of the bottom surface being recessed from the locking portion of the bottom surface to define a cavity;
a lock element including a receiver having spaced arms that define a portion an implant cavity, the receiver comprising a raised portion between the arms and a cylindrical shaft that extends from the raised portion, end surfaces of the arms engaging the bottom surface such that the raised portion is nested within the cavity, the shaft comprising a threaded portion and a non-threaded portion that is positioned within the passageway, an inner surface of the non-threaded portion defining a portion of the implant cavity; and
a nut comprising a body having an end surface that engages the top surface, the body comprising a threaded cavity that extends through the end surface, the threaded portion being disposed in the threaded cavity, the nut comprising a flange that extends from the body, the flange being configured to break off from the body.

* * * * *

UNITED STATES PATENT AND TRADEMARK OFFICE
CERTIFICATE OF CORRECTION

PATENT NO. : 9,848,920 B2
APPLICATION NO. : 14/248079
DATED : December 26, 2017
INVENTOR(S) : Mirda It is certified that error appears in the above-identified patent and that said Letters Patent is hereby corrected as shown below:

In the Specification

In Column 3, Line 61, delete "Inc.)" and insert -- Inc.), --, therefor.

In Column 3, Line 64, delete "PEEK-BaS0$_4$" and insert -- PEEK-BaSO$_4$ --, therefor.

In Column 5, Line 9, delete "dosed" and insert -- closed --, therefor.

In Column 7, Line 39, delete "plot" and insert -- pilot --, therefor.

In Column 8, Line 5, delete "flange 90" and insert -- flange 92 --, therefor.

In Column 8, Line 12, delete "dosed." and insert -- closed. --, therefor.

In Column 8, Line 34, delete "dips," and insert -- clips, --, therefor.

Signed and Sealed this
Third Day of April, 2018

Andrei Iancu
*Director of the United States Patent and Trademark Office*